US010039901B2

(12) United States Patent
Warnking

(10) Patent No.: US 10,039,901 B2
(45) Date of Patent: Aug. 7, 2018

(54) METHOD AND APPARATUS FOR TREATMENT OF HYPERTENSION THROUGH PERCUTANEOUS ULTRASOUND RENAL DENERVATION

(71) Applicant: ReCor Medical, Inc., Palo Alto, CA (US)

(72) Inventor: Richard J. Warnking, East Setauket, NY (US)

(73) Assignee: ReCor Medical, Inc., Palo Alto, CA (US)

(*) Notice: Subject to any disclaimer, the term of this patent is extended or adjusted under 35 U.S.C. 154(b) by 0 days.

(21) Appl. No.: 13/826,645

(22) Filed: Mar. 14, 2013

(65) Prior Publication Data
US 2014/0031727 A1 Jan. 30, 2014

Related U.S. Application Data

(63) Continuation of application No. 13/503,109, filed as application No. PCT/US2010/054637 on Oct. 29, 2010.
(Continued)

(51) Int. Cl.
A61M 25/00 (2006.01)
A61M 25/10 (2013.01)
(Continued)

(52) U.S. Cl.
CPC .... *A61M 25/0082* (2013.01); *A61M 25/1002* (2013.01); *A61N 7/00* (2013.01);
(Continued)

(58) Field of Classification Search
CPC ...... A61M 25/0108; A61M 2205/3693; A61N 7/02; A61N 1/08
See application file for complete search history.

(56) References Cited

U.S. PATENT DOCUMENTS 4,841,977 A 6/1989 Griffith et al.
5,295,992 A * 3/1994 Cameron .................. 606/79
(Continued)

FOREIGN PATENT DOCUMENTS

DE 20 2005 022 060 U1 11/2012
EP 0 623 360 B1 11/1994
(Continued)

OTHER PUBLICATIONS onlinemathlearning.com,"Volume of a Hollow Cylinder".*
(Continued)

*Primary Examiner* — Tse Chen
*Assistant Examiner* — Joanne Hoffman
(74) *Attorney, Agent, or Firm* — Foley & Lardner LLP; Christopher C. Bolten; Nicola A. Pisano

(57) ABSTRACT

Apparatus and methods for deactivating renal nerves extending along a renal artery of a mammalian subject to treat hypertension and related conditions. An ultrasonic transducer (30) is inserted into the renal artery (10) as, for example, by advancing the distal end of a catheter (18) bearing the transducer into the renal artery. The ultrasonic transducer emits unfocused ultrasound so as to heat tissues throughout a relatively large impact volume (11) as, for example, at least about 0.5 cm$^3$ encompassing the renal artery to a temperature sufficient to inactivate nerve conduction but insufficient to cause rapid ablation or necrosis of the tissues. The treatment can be performed without locating or focusing on individual renal nerves.

22 Claims, 7 Drawing Sheets

Related U.S. Application Data

(60) Provisional application No. 61/256,429, filed on Oct. 30, 2009, provisional application No. 61/292,618, filed on Jan. 6, 2010.

(51) Int. Cl.
*A61N 7/00* (2006.01)
*A61N 7/02* (2006.01)
*A61B 17/00* (2006.01)
*A61B 17/22* (2006.01)
*A61B 18/00* (2006.01)

(52) U.S. Cl.
CPC ........ *A61N 7/022* (2013.01); *A61B 2017/003* (2013.01); *A61B 2017/00323* (2013.01); *A61B 2017/22021* (2013.01); *A61B 2018/00023* (2013.01); *A61M 25/0068* (2013.01); *A61M 2025/1047* (2013.01); *A61M 2025/1068* (2013.01); *A61M 2025/1086* (2013.01); *A61M 2025/1093* (2013.01); *A61N 2007/0026* (2013.01); *A61N 2007/0043* (2013.01)

(56) References Cited

U.S. PATENT DOCUMENTS

| | | | |
|---|---|---|---|
| 5,295,995 A | 3/1994 | Kleiman | |
| 5,308,356 A | 5/1994 | Blackshear et al. | |
| 5,324,255 A | 6/1994 | Passafaro et al. | |
| 5,327,885 A | 7/1994 | Griffith | |
| 5,400,267 A | 3/1995 | Denen et al. | |
| 5,423,220 A | 6/1995 | Finsterwald et al. | |
| 5,456,259 A | 10/1995 | Barlow et al. | |
| 5,524,491 A | 6/1996 | Cavalloni | |
| 5,620,479 A | 4/1997 | Dieferich | |
| 5,630,837 A | 5/1997 | Crowley | |
| 5,713,849 A | 2/1998 | Bosma et al. | |
| 5,769,812 A | 6/1998 | Stevens et al. | |
| 5,775,338 A * | 7/1998 | Hastings ................ | 128/898 |
| 5,803,083 A | 9/1998 | Buck et al. | |
| 6,097,985 A * | 8/2000 | Kasevich et al. ............ | 607/102 |
| 6,102,863 A * | 8/2000 | Pflugrath et al. ............ | 600/447 |
| 6,117,101 A | 9/2000 | Dieder et al. | |
| 6,128,522 A | 10/2000 | Acker et al. | |
| 6,149,596 A * | 11/2000 | Bancroft ................ | 600/439 |
| 6,190,377 B1 * | 2/2001 | Kuzdrall ................ | 606/10 |
| 6,216,704 B1 | 4/2001 | Ingle et al. | |
| 6,277,077 B1 | 8/2001 | Brisken et al. | |
| 6,299,583 B1 * | 10/2001 | Eggers et al. ................ | 600/526 |
| 6,355,030 B1 | 3/2002 | Aldrich et al. | |
| 6,475,146 B1 | 11/2002 | Frelburger et al. | |
| 6,492,762 B1 | 12/2002 | Pant et al. | |
| 6,517,534 B1 * | 2/2003 | McGovern et al. ............ | 606/41 |
| 6,599,256 B1 | 7/2003 | Acker et al. | |
| 6,635,054 B2 | 10/2003 | Fjield et al. | |
| 6,645,202 B1 | 11/2003 | Pless et al. | |
| 6,763,722 B2 | 7/2004 | Fjield et al. | |
| 6,793,635 B2 | 9/2004 | Ryan et al. | |
| 6,913,581 B2 | 7/2005 | Corl et al. | |
| 6,953,469 B2 | 10/2005 | Ryan | |
| 6,978,174 B2 | 12/2005 | Gelfand et al. | |
| 7,162,303 B2 | 1/2007 | Levin et al. | |
| 7,285,116 B2 | 10/2007 | de la Rama et al. | |
| 7,347,852 B2 | 3/2008 | Hobbs et al. | |
| 7,473,224 B2 | 1/2009 | Makin | |
| 7,540,846 B2 | 6/2009 | Harhen et al. | |
| 7,617,005 B2 | 11/2009 | Demarais et al. | |
| 7,620,451 B2 | 11/2009 | Demarais et al. | |
| 7,625,371 B2 | 12/2009 | Morris et al. | |
| 7,647,115 B2 | 1/2010 | Levin et al. | |
| 7,653,438 B2 | 1/2010 | Deem et al. | |
| 7,678,104 B2 | 3/2010 | Keidar | |
| 7,717,948 B2 | 5/2010 | Demarais et al. | |
| 7,756,583 B2 | 7/2010 | Demarais et al. | |
| 7,756,683 B2 | 7/2010 | Kilgus | |
| 7,837,676 B2 | 11/2010 | Sinelnikov et al. | |
| 7,846,317 B2 | 12/2010 | Meltzer et al. | |
| 7,873,417 B2 | 1/2011 | Demarais et al. | |
| 7,937,143 B2 | 5/2011 | Demarais et al. | |
| 8,131,371 B2 | 3/2012 | Demarals et al. | |
| 8,233,221 B2 | 7/2012 | Suijver et al. | |
| 8,251,986 B2 | 8/2012 | Chornenky et al. | |
| 8,287,472 B2 | 10/2012 | Ostrovsky et al. | |
| 8,475,442 B2 | 7/2013 | Hall et al. | |
| 8,485,993 B2 | 7/2013 | Orszulak et al. | |
| 8,504,147 B2 | 8/2013 | Deem et al. | |
| D697,036 S | 1/2014 | Kay et al. | |
| 8,715,209 B2 | 5/2014 | Gertner | |
| 8,734,438 B2 | 5/2014 | Behnke | |
| D708,810 S | 7/2014 | Lewis, Jr. | |
| 8,808,345 B2 | 8/2014 | Clark et al. | |
| D712,352 S | 9/2014 | George et al. | |
| D712,353 S | 9/2014 | George et al. | |
| D712,833 S | 9/2014 | George et al. | |
| 8,974,445 B2 | 3/2015 | Warnking et al. | |
| 2001/0007940 A1 | 7/2001 | Tu et al. | |
| 2002/0002334 A1 * | 1/2002 | Okuno et al. ................ | 600/443 |
| 2002/0002371 A1 | 1/2002 | Acker et al. | |
| 2002/0065512 A1 | 5/2002 | Fjield et al. | |
| 2002/0087156 A1 | 7/2002 | Maguire et al. | |
| 2002/0150693 A1 | 10/2002 | Kobayashi et al. | |
| 2002/0151889 A1 | 10/2002 | Swanson et al. | |
| 2002/0165535 A1 * | 11/2002 | Lesh ................ | A61B 17/2202 |
| | | | 606/41 |
| 2002/0193781 A1 * | 12/2002 | Loeb ................ | 606/15 |
| 2003/0060813 A1 * | 3/2003 | Loeb et al. ................ | 606/17 |
| 2003/0138571 A1 | 7/2003 | Kunishi et al. | |
| 2003/0181963 A1 | 9/2003 | Pellegrino et al. | |
| 2003/0204138 A1 | 10/2003 | Choi | |
| 2003/0216721 A1 | 11/2003 | Diederich et al. | |
| 2003/0216792 A1 | 11/2003 | Levin et al. | |
| 2003/0216794 A1 | 11/2003 | Becker et al. | |
| 2003/0225331 A1 | 12/2003 | Diederich et al. | |
| 2003/0233099 A1 | 12/2003 | Danaek et al. | |
| 2004/0044286 A1 | 3/2004 | Hossack et al. | |
| 2004/0082859 A1 | 4/2004 | Schaer | |
| 2004/0167415 A1 * | 8/2004 | Gelfand ........... | A61B 17/12036 |
| | | | 600/500 |
| 2004/0230116 A1 * | 11/2004 | Cowan et al. ................ | 600/437 |
| 2004/0253450 A1 | 12/2004 | Seita et al. | |
| 2005/0009218 A1 | 1/2005 | Kunihiro | |
| 2005/0035901 A1 * | 2/2005 | Lyon ................ | 342/124 |
| 2005/0215990 A1 | 9/2005 | Govari | |
| 2005/0234523 A1 | 10/2005 | Levin et al. | |
| 2005/0256518 A1 | 11/2005 | Rama et al. | |
| 2005/0288730 A1 | 12/2005 | Deem et al. | |
| 2006/0041277 A1 | 2/2006 | Deem et al. | |
| 2006/0058711 A1 | 3/2006 | Harhen et al. | |
| 2006/0064081 A1 | 3/2006 | Rosinko | |
| 2006/0088705 A1 | 4/2006 | Mitsumori | |
| 2006/0100514 A1 | 5/2006 | Lopath | |
| 2006/0121200 A1 | 6/2006 | Halpert et al. | |
| 2006/0154072 A1 | 7/2006 | Schlossman et al. | |
| 2006/0155269 A1 | 7/2006 | Warnking | |
| 2006/0184072 A1 | 8/2006 | Manna | |
| 2006/0212076 A1 | 9/2006 | Demarais et al. | |
| 2006/0212078 A1 | 9/2006 | Demarais et al. | |
| 2006/0229594 A1 | 10/2006 | Francischello et al. | |
| 2006/0241523 A1 | 10/2006 | Sinelnikov et al. | |
| 2006/0265014 A1 | 11/2006 | Demarais et al. | |
| 2006/0265015 A1 | 11/2006 | Demarais et al. | |
| 2006/0270976 A1 | 11/2006 | Savage et al. | |
| 2006/0276852 A1 | 12/2006 | Demarais et al. | |
| 2007/0124458 A1 | 5/2007 | Kumar | |
| 2007/0129720 A1 | 6/2007 | Demarais et al. | |
| 2007/0129760 A1 | 6/2007 | Demarais et al. | |
| 2007/0135875 A1 * | 6/2007 | Demarais et al. ............ | 607/96 |
| 2007/0173899 A1 | 7/2007 | Levin et al. | |
| 2007/0203547 A1 | 8/2007 | Costello et al. | |
| 2007/0203549 A1 * | 8/2007 | Demarais ................ | A61N 1/05 |
| | | | 607/72 |
| 2007/0255267 A1 * | 11/2007 | Diederich et al. ............ | 606/27 |
| 2007/0255342 A1 * | 11/2007 | Laufer ................ | A61B 18/14 |
| | | | 607/48 |

(56) References Cited

U.S. PATENT DOCUMENTS

| | | |
|---|---|---|
| 2007/0265609 A1 | 11/2007 | Thapliyal et al. |
| 2007/0265610 A1 | 11/2007 | Thapliyal et al. |
| 2007/0265687 A1 | 11/2007 | Deem et al. |
| 2007/0282407 A1 | 12/2007 | Demarais et al. |
| 2007/0293762 A1 | 12/2007 | Sawada et al. |
| 2008/0052186 A1 | 2/2008 | Walker et al. |
| 2008/0151001 A1 | 6/2008 | Sudo et al. |
| 2008/0255449 A1 | 10/2008 | Warnking et al. |
| 2008/0255478 A1 | 10/2008 | Burdette |
| 2008/0255642 A1 | 10/2008 | Zarins et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0118125 A1 | 5/2009 | Kobayashi et al. |
| 2009/0124964 A1 | 5/2009 | Leach et al. |
| 2009/0149753 A1 | 6/2009 | Govari et al. |
| 2009/0171202 A1 | 7/2009 | Kirkpatrick et al. |
| 2009/0189485 A1 | 7/2009 | Iyoki |
| 2009/0204006 A1 | 8/2009 | Wakabayashi et al. |
| 2009/0221939 A1 | 9/2009 | Demarais et al. |
| 2009/0228003 A1 | 9/2009 | Sinelnikov |
| 2009/0248011 A1 | 10/2009 | Hlavka et al. |
| 2009/0299360 A1 | 12/2009 | Ormsby |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0033940 A1 | 2/2010 | Yamaguchi et al. |
| 2010/0049099 A1 | 2/2010 | Thapliyal et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0152582 A1 | 6/2010 | Thapliyal et al. |
| 2010/0168731 A1 | 7/2010 | Wu et al. |
| 2010/0168737 A1 | 7/2010 | Grunewald |
| 2010/0168739 A1 | 7/2010 | Wu et al. |
| 2010/0174282 A1 | 7/2010 | Demarais et al. |
| 2010/0179424 A1 | 7/2010 | Warnking et al. |
| 2010/0189974 A1 | 7/2010 | Ochi et al. |
| 2010/0191112 A1 | 7/2010 | Demarais et al. |
| 2010/0198065 A1 | 8/2010 | Thapliyal et al. |
| 2010/0249859 A1 | 9/2010 | Dilorenzo |
| 2011/0004184 A1 | 1/2011 | Proksch et al. |
| 2011/0060324 A1 | 3/2011 | Wu et al. |
| 2011/0087096 A1 | 4/2011 | Behar |
| 2011/0087097 A1 | 4/2011 | Behar |
| 2011/0104060 A1 | 5/2011 | Seward |
| 2011/0112400 A1 | 5/2011 | Emery et al. |
| 2011/0118598 A1 | 5/2011 | Gertner |
| 2011/0137298 A1 | 6/2011 | Nguyen et al. |
| 2011/0172527 A1 | 7/2011 | Gertner |
| 2011/0178516 A1 | 7/2011 | Orszulak et al. |
| 2011/0200171 A1 | 8/2011 | Beetel et al. |
| 2011/0208096 A1 | 8/2011 | Demarais et al. |
| 2011/0257523 A1 | 10/2011 | Hastings et al. |
| 2011/0257562 A1 | 10/2011 | Schaer |
| 2011/0257563 A1 | 10/2011 | Thapliyal et al. |
| 2011/0257564 A1 | 10/2011 | Demarais et al. |
| 2011/0301662 A1 | 12/2011 | Bar-Yoseph et al. |
| 2011/0319765 A1 | 12/2011 | Gertner et al. |
| 2012/0004656 A1 | 1/2012 | Jackson et al. |
| 2012/0065493 A1 | 3/2012 | Gertner |
| 2012/0065554 A1 | 3/2012 | Pikus |
| 2012/0078278 A1 | 3/2012 | Bales et al. |
| 2012/0095461 A1 | 4/2012 | Herscher et al. |
| 2012/0123243 A1 | 5/2012 | Hastings |
| 2012/0123303 A1 | 5/2012 | Sogard et al. |
| 2012/0143097 A1 | 6/2012 | Pike, Jr. |
| 2012/0165667 A1 | 6/2012 | Altmann et al. |
| 2012/0172723 A1 | 7/2012 | Gertner |
| 2012/0215106 A1 | 8/2012 | Sverdlik et al. |
| 2012/0232436 A1 | 9/2012 | Warnking |
| 2012/0238918 A1 | 9/2012 | Gertner |
| 2012/0238919 A1 | 9/2012 | Gertner |
| 2012/0265198 A1 | 10/2012 | Crow et al. |
| 2012/0316439 A1 | 12/2012 | Behar |
| 2013/0012844 A1 | 1/2013 | Demarais et al. |
| 2013/0072928 A1 | 3/2013 | Schaer |
| 2013/0090650 A1 | 4/2013 | Jenson et al. |
| 2013/0103064 A1 | 4/2013 | Arenson et al. |
| 2013/0110012 A1 | 5/2013 | Gertner |
| 2013/0131668 A1 | 5/2013 | Schaer |
| 2013/0138018 A1 | 5/2013 | Gertner |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165924 A1 | 6/2013 | Mathur et al. |
| 2013/0197555 A1 | 8/2013 | Schaer |
| 2013/0204167 A1 | 8/2013 | Sverdlik et al. |
| 2013/0211396 A1 | 8/2013 | Sverdlik et al. |
| 2013/0218054 A1 | 8/2013 | Sverdlik et al. |
| 2013/0274658 A1 | 10/2013 | Steinke et al. |
| 2013/0282084 A1 | 10/2013 | Mathur et al. |
| 2013/0304047 A1 | 11/2013 | Grunewald et al. |
| 2013/0331739 A1 | 12/2013 | Gertner |
| 2014/0012133 A1 | 1/2014 | Sverdlik et al. |
| 2014/0018794 A1 | 1/2014 | Anderson et al. |
| 2014/0025069 A1 | 1/2014 | Willard et al. |
| 2014/0031727 A1 | 1/2014 | Warnking |
| 2014/0039477 A1 | 2/2014 | Sverdlik et al. |
| 2014/0046313 A1 | 2/2014 | Pederson et al. |
| 2014/0067029 A1 | 3/2014 | Schauer et al. |
| 2014/0074083 A1 | 3/2014 | Horn et al. |
| 2014/0107639 A1 | 4/2014 | Zhang et al. |
| 2014/0163540 A1 | 6/2014 | Iyer et al. |
| 2014/0180196 A1 | 6/2014 | Stone et al. |
| 2014/0180197 A1 | 6/2014 | Sverdlik et al. |
| 2014/0194785 A1 | 7/2014 | Gertner |
| 2014/0200489 A1 | 7/2014 | Behar et al. |
| 2014/0214018 A1 | 7/2014 | Behar et al. |
| 2014/0249524 A1 | 9/2014 | Kocur |
| 2014/0272110 A1 | 9/2014 | Taylor et al. |
| 2014/0275924 A1 | 9/2014 | Min et al. |
| 2014/0276742 A1 | 9/2014 | Nabutovsky et al. |
| 2014/0276752 A1 | 9/2014 | Wang et al. |
| 2014/0276755 A1 | 9/2014 | Cao et al. |
| 2014/0276789 A1 | 9/2014 | Dandler et al. |
| 2014/0277033 A1 | 9/2014 | Taylor et al. |
| 2015/0223877 A1 | 8/2015 | Behar et al. |
| 2015/0290427 A1 | 10/2015 | Warnking |
| 2015/0335919 A1 | 11/2015 | Behar et al. |
| 2016/0016016 A1 | 1/2016 | Taylor et al. |

FOREIGN PATENT DOCUMENTS

| | | |
|---|---|---|
| EP | 0 767 630 B1 | 4/1997 |
| EP | 0 838 980 A2 | 4/1998 |
| EP | 1 100 375 B1 | 5/2001 |
| EP | 1 384 445 A1 | 1/2004 |
| EP | 1384445 | 1/2004 |
| EP | 1 647 305 B1 | 4/2006 |
| EP | 2 218 479 A2 | 8/2010 |
| EP | 2218479 A2 | 8/2010 |
| EP | 2 457 614 A1 | 5/2012 |
| EP | 2 460 486 B1 | 6/2012 |
| EP | 2 495 012 A1 | 9/2012 |
| EP | 2 521 593 B1 | 11/2012 |
| EP | 2 561 903 A1 | 2/2013 |
| EP | 2 561 905 A1 | 2/2013 |
| EP | 2 626 022 A2 | 8/2013 |
| EP | 2 632 373 | 9/2013 |
| EP | 2 662 041 A2 | 11/2013 |
| EP | 2 662 043 A2 | 11/2013 |
| JP | 05-068684 A | 3/1993 |
| JP | 40-826437 A | 10/1996 |
| JP | 2000-054153 A | 2/2000 |
| JP | 2005-526579 A | 9/2005 |
| JP | 2008-515544 | 5/2008 |
| JP | 2008-515544 A1 | 5/2008 |

(56) References Cited

FOREIGN PATENT DOCUMENTS

| | | |
|---|---|---|
| JP | 2008-214669 A | 9/2008 |
| JP | 2010-503466 A1 | 2/2010 |
| WO | WO-00/41881 A2 | 7/2000 |
| WO | WO-03/059437 A2 | 7/2003 |
| WO | WO-03/099382 A1 | 12/2003 |
| WO | WO-2005/009218 A2 | 2/2005 |
| WO | WO-2006/041847 A1 | 4/2006 |
| WO | WO-2006/041881 A2 | 4/2006 |
| WO | WO2006041847 | 4/2006 |
| WO | WO2006041881 | 4/2006 |
| WO | WO-2006/060053 A2 | 6/2006 |
| WO | WO-2007/124458 A2 | 11/2007 |
| WO | WO-2007/135875 | 11/2007 |
| WO | WO-2007/135875 A1 | 11/2007 |
| WO | WO-2007/146834 A2 | 12/2007 |
| WO | WO-2008/036479 A2 | 3/2008 |
| WO | WO-2008/052186 A2 | 5/2008 |
| WO | WO-2008/061152 A2 | 5/2008 |
| WO | WO-2008/151001 A2 | 12/2008 |
| WO | WO2008151001 A2 | 12/2008 |
| WO | WO-2009/149315 A2 | 12/2009 |
| WO | WO-2010/033940 A1 | 3/2010 |
| WO | WO-2010/067360 A2 | 6/2010 |
| WO | WO-2011/046880 A2 | 4/2011 |
| WO | WO-2011/053757 A1 | 5/2011 |
| WO | WO-2011/082279 A2 | 7/2011 |
| WO | WO-2011/088399 A1 | 7/2011 |
| WO | WO-2011/094367 A1 | 8/2011 |
| WO | WO-2011/139589 A2 | 11/2011 |
| WO | WO-2012/112165 A1 | 8/2012 |

OTHER PUBLICATIONS

U.S. Appl. No. 12/685,655, filed Jan. 11, 2010.
U.S. Appl. No. 12/725,450, filed Mar. 16, 2010.
Bhatt, et al., A Controlled Trial of Renal Denervation for Resistant Hypertension, N. Engl. J. Med., 370:1393-1401 (2014).
Bunch, Jared, et al., Mechanisms of Phrenic Nerve Injury During Radiofrequency Ablation at the Pulmonary Vein Orifice, Journal of Cardiovascular Electrophysiology, 16(12):1318-1325 (2005).
Campese, et al., Renal afferent denervation prevents hypertension in rats with chronic renal failure, Hypertension, 25:878-882 (1995).
Dibona, Renal nerves in compensatory renal response to contralateral renal denervation, Renal Physiology, 238 (1):F26-F30 (1980).
International Search Report & Written Opinion dated Jul. 9, 2014 in Int'l PCT Patent Application Serial No. PCT/US2014/22804.
International Search Report & Written Opinion dated Nov. 29, 2011 in Int'l PCT Patent Application Serial No. PCT/US2011/025543.
International Search Report dated Feb. 9, 2014 in Intl PCT Patent Application Serial No. PCT/US2014/022796.
Medtronic Press Release, Jan. 9, 2014, Medtronic Announces U.S. Renal Denervation Pivotal Trial Fails to Meet Primary Efficacy Endpoint While Meeting Primary Safety Endpoint.
Oliveira, et a., Renal Denervation Normalizes Pressure and Baroreceptor Reflex in High Renin Hypertension in Conscious Rats, Hypertension 19:17-21 (1992).
Smithwick, R.H., Surgery in hypertension, Lancet, 2:65 (1948).
Smithwick, R.H., Surgical treatment of hypertension, Am J Med 4:744-759 (1948).
www.dictionary.com/browse/degrease, retrieved Jun. 7, 2016.
OnlineMathLearning.com, "Volume of a Hollow Cylinder" Sep. 22, 2008.
Wang, S., et al., Effects of Low Intensity Ultrasound on the Conduction Property of Neural Tissues, IEEE International Ultrasonics, Ferroelectrics, and Frequency Control, Joint 50th Anniversary Conference, 2004.

\* cited by examiner

METHOD AND APPARATUS FOR TREATMENT OF HYPERTENSION THROUGH PERCUTANEOUS ULTRASOUND RENAL DENERVATION

CROSS-REFERENCE TO RELATED APPLICATIONS

This application is a continuation of application Ser. No. 13/503,109 filed Apr. 20, 2012, which is a national phase of International Application No. PCT/2010/54637 filed Oct. 29, 2010. This application claims the benefit of the filing date of US Provisional Patent Application Nos. 61/256,429, filed on Oct. 30, 2009, and 61/292,618, filed on Jan. 6, 2010, the disclosures of which are hereby incorporated herein by reference.

BACKGROUND OF THE INVENTION

Successful treatment of hypertension is important for many reasons. For example, successful treatment of hypertension has significant clinical benefits in preventing or limiting conditions caused by or exacerbated by hypertension, such as renal disease, arrhythmias, and congestive heart failure, to name a few. While drug therapy can be used to treat hypertension, it is not always successful. Some people are resistant to drug therapy treatment or experience significant side effects from drug therapy treatment.

Hypertension can be treated by inactivating conduction of the renal nerves surrounding the renal artery. Sympathetic renal nerve activity plays a significant role in the initiation and maintenance of hypertension. When the brain perceives increased renal nerve activity, signaling low blood volume or a drop in blood pressure, it compensates by increasing sympathetic nerve activity to the heart, the liver, and the kidneys, which results in increased cardiac output; insulin resistance; and most importantly, increased renin production by the kidneys. Renin stimulates the production of angiotension, which causes blood vessels to constrict, resulting in increased blood pressure and stimulates the secretion of aldosterone. Aldosterone causes the kidneys to increase the reabsorption of sodium and water into the blood, increasing blood volume thereby further increasing blood pressure.

It has been established for years that surgically cutting renal nerves results in a decrease in blood pressure and water retention to normal levels; thereby allowing the patients' heart, liver, and kidneys to also return to healthier functioning. It has also been shown a disruption of the renal nerves has no serious ill effects. However, surgically cutting the renal nerves requires a major surgical procedure with risks of undesirable side effects. It would be desirable to produce the same result without major surgery.

In order to explain the difficulties associated with accomplishing this task without causing other damage, the anatomy of the renal arteries and nerves will be described now. Shown in FIG. 1 is an illustration of the renal nerves 8 that surround the renal artery 10, which is connected to the kidney 6. The sympathetic renal nerves 8 include both the afferent sensory renal nerves from the kidney 6 to the brain and the efferent sympathetic renal nerves from the brain to the kidney 6. In addition, FIG. 2 shows a cross-section of a renal artery 10. The renal artery wall includes layers: the intima 3, which includes an inner single layer of endothelial cells; the media 5, which is in the center of the artery wall; and the adventitia 4, which is the outside layer. Also shown are the renal nerves 8 that lie within the aventitia 4, on the surface of the renal artery 10, and adjacent to the renal artery 10. As can be seen from these two figures, the renal nerves 8 surround the renal artery 10. Different individuals have the renal nerves 8 in different locations around the renal artery. Thus, the renal nerves may be at different radial distances R from the central axis A of the renal artery, and also may be at different locations around the circumference C of the renal artery. It is not practical to locate the renal nerves by referring to anatomical landmarks. Moreover, it is difficult or impossible to locate individual renal nerves using common in vivo imaging technology.

The inability to locate and target the renal nerves 8 makes it difficult to disconnect the sympathetic renal activity using non-surgical techniques without causing damage to the renal artery 10 or causing other side effects. For example, attempts to apply energy to the renal nerves can cause effects such as stenosis, intimal hyperplasia, and necrosis. Other side effects can include thrombosis, platelet aggregation, fibrin clots and vasoconstriction. In addition, the inability to target and locate the renal nerves 8 makes it difficult to ensure that sympathetic renal nerve activity has been discontinued enough to achieve an acceptable therapeutic treatment.

U.S. Pat. No. 7,617,005 suggests the use of a radio frequency ("RF") emitter connected to a catheter, which is inserted in the renal artery. The RF emitter is placed against the intima and the RF energy is emitted to heat the renal nerves to a temperature that reduces the activity of renal nerves which happen to lie in the immediate vicinity of the emitter. In order to treat all the renal nerves surrounding the renal arteries, the RF emitter source must be repositioned around the inside of each renal artery multiple times. The emitter may miss some of the renal nerves, leading to an incomplete treatment. Moreover, the RF energy source must contact the intima to be able to heat the renal nerves, which may cause damage or necrosis to the single layer endothelium and the intima, potentially causing intimal hyperplasia, renal artery stenosis, and renal artery dissection.

The '005 Patent also suggests the use of high-intensity focused ultrasound to deactivate the renal nerves. The described high-intensity focused ultrasound energy source assertedly emits ultrasound energy in a 360° pattern around the axis of the renal artery, and does not need to contact the intima 3. However, the high-intensity focused ultrasound source applies concentrated energy in a thin focal ring surrounding the artery. It is difficult or impossible to align this thin ring with the renal nerves because it is difficult or impossible to visualize and target the renal nerves with current technology, and because the renal nerves may lie at different radial distances from the central axis of the renal artery. The latter problem is aggravated in patients who have renal arteries with large variations in shape or thickness. Moreover, the thin focal ring can encompass only a small segment of each renal nerve along the lengthwise direction of the nerves and artery. Since nerves tend to re-grow, a small treatment zone allows the nerves to reconnect in a shorter period of time.

For many years ultrasound has been used to enhance cell repair, stimulate the growth of bone cells, enhance delivery of drugs to specific tissues, and to image tissue within the body. In addition, high-intensity focused ultrasound has been used to heat and ablate tumors and tissue within the body. Ablation of tissue has been performed nearly exclusively by high-intensity focused ultrasound because the emitted ultrasound energy is focused on a specific location to allow precise in-depth tissue necrosis without affecting surrounding tissue and intervening structures that the ultrasound energy must pass through.

U.S. Pat. No. 6,117,101, to Diederich, discusses use of highly collimated ultrasound energy rather than high intensity focused ultrasound for ablating tissue to create a scar ring within the pulmonary vein for blocking the conduction of electrical signals to the heart.

US Patent Publication No. 20100179424 (application Ser. No. 12/684,067), the disclosure of which is incorporated by reference herein, uses unfocused ultrasound for the treatment of mitral valve regurgitation. In the '474 Publication, unfocused ultrasound energy is used to heat and shrink the collagen associated with the mitral annulus. This apparatus uses an inflatable balloon in order to place the ultrasound transducer into the correct location, thereby targeting the mitral annulus. In this apparatus, a part of the balloon contacts the tissue to be heated.

BRIEF SUMMARY OF THE INVENTION

One aspect of the invention provides apparatus for inactivating renal nerve conduction in a human or non-human mammalian subject. The apparatus according to this aspect of the invention preferably includes an ultrasound transducer adapted for insertion into a renal artery of the mammalian subject. The ultrasound transducer desirably is arranged to transmit unfocused ultrasound energy. The apparatus according to this aspect of the invention desirably also includes an actuator electrically connected to the transducer. The actuator most preferably is adapted to control the ultrasound transducer to transmit unfocused ultrasound energy into an impact volume of at least approximately 0.5 $cm^3$, encompassing the renal artery so that the unfocused ultrasound energy is applied at a therapeutic level sufficient to inactivate conduction of renal nerves throughout the impact volume. As discussed further below, such therapeutic level is below the level required for tissue ablation.

The apparatus may further include a catheter with a distal end and a proximal end, the transducer being mounted to the catheter adjacent the distal end, the catheter and transducer being constructed and arranged to allow a substantial flow of blood through the renal artery while the ultrasound transducer is positioned within the renal artery. The catheter may be constructed and arranged to hold the transducer out of contact with the wall of the renal artery. The catheter may have an expansible element such as a balloon, wire basket or the like mounted adjacent the distal end. For example, the transducer may be adapted to transmit the ultrasound energy in a 360° cylindrical pattern surrounding a transducer axis, and the catheter may be constructed and arranged to hold the axis of the transducer generally parallel to the axis of the renal artery.

A further aspect of the invention provides methods for inactivating renal nerve conduction in a mammalian subject. A method according to this aspect of the invention desirably includes the steps of inserting an ultrasound transducer into a renal artery of the subject and actuating the transducer to transmit therapeutically effective unfocused ultrasound energy into an impact volume of at least approximately 0.5 $cm^3$ encompassing the renal artery. The ultrasound energy desirably is applied so that the therapeutically effective unfocused ultrasound energy inactivates conduction of all the renal nerves in the impact volume. For example, the step of actuating the transducer may be so as to maintain the temperature of the renal artery wall below 65° C. while heating the solid tissues within the impact volume, including the renal nerves in the impact volume, to above 42° C.

Because the impact volume is relatively large, and because the tissues throughout the impact volume preferably reach temperatures sufficient to inactivate nerve conduction, the preferred methods according to this aspect of the invention can be performed successfully without determining the actual locations of the renal nerves, and without targeting or focusing on the renal nerves. The treatment can be performed without measuring the temperature of tissues. Moreover, the treatment preferably is performed without causing stenosis of the renal artery, intimal hyperplasia, or other injuries that would require intervention. The preferred methods and apparatus can inactive relatively long segments of the renal nerves, so as to reduce the possibility of nerve recovery which would re-establish conduction along the inactivated segments.

Further aspects of the invention provide probes which can be used in the method and apparatus discussed above, and apparatus incorporating means for performing the steps of the methods discussed above.

DETAILED DESCRIPTION

Figure 1:
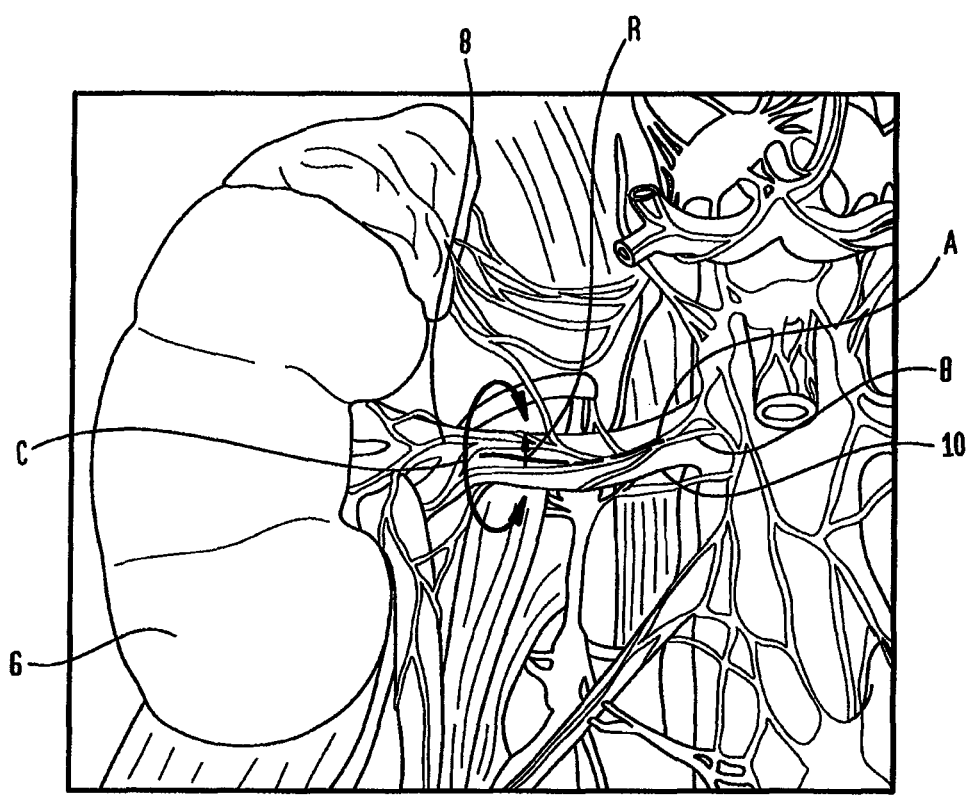
FIG. 1 is an anatomical view of a typical renal artery and associated structure.

Apparatus invention (FIG. 3) At least one embodiment includes a sheath 12. The sheath 12 generally may be in the form of an elongated tube having a proximal end 14, a distal end 16 and a proximal-to-distal axis 15. As used in this disclosure with reference to elongated elements for insertion into the body, the term "distal" refers to the end which is inserted into the body first, i.e., the leading end during advancement of the element into the body, whereas the term "proximal" refers to the opposite end. The sheath 12 may be a steerable sheath. Thus, the sheath may include known elements such as one or more pull wires (not shown) extending between the proximal and distal ends of the sheath and connected to a steering control 17 arranged so that actuation of the steering control by the operator flexes the distal end 16 of the sheath in a direction transverse to the axis 15.

Figure 3:
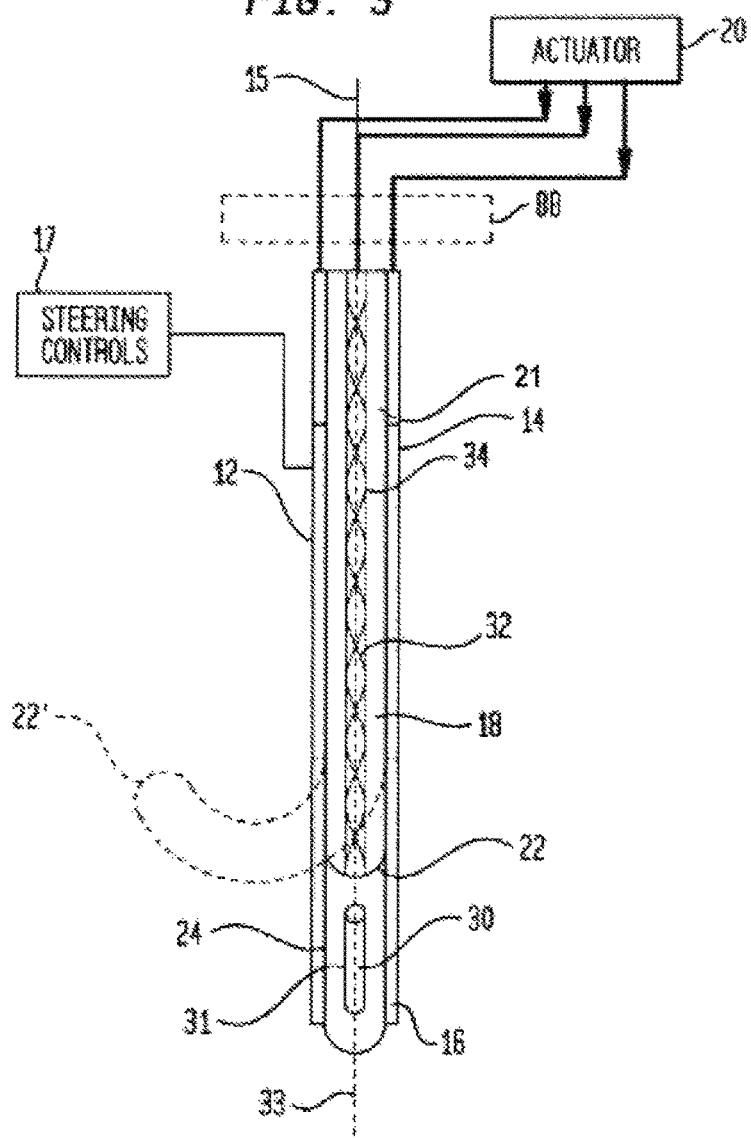
FIG. 3 is a diagrammatic view depicting components of apparatus in accordance with one embodiment of the present invention.

The apparatus also includes a catheter 18 having a proximal end 21, a distal end 22 and a proximal-to-distal axis which, in the condition depicted in FIG. 3, is coincident with the proximal-to-distal axis 15 of the sheath. The proximal end 21 of the catheter desirably is relatively stiff such that it may transmit torque. Thus, by turning the proximal end 21 of the catheter 18, distal end 22 of the catheter 18 can be rotated about the proximal-to-distal axis of the catheter 18.

The distal end 22 of the catheter 18 is preformed so that when the distal end of the catheter is outside of the sheath 12, the distal end tends to assume a hooked configuration as indicated in broken lines at 22' in FIG. 3. In this condition, rotational motion of the distal end 22' will swing the curved section around the proximal-to-distal axis. Thus, by rotating the proximal end of the catheter 18, the distal end 22' of the catheter 18 can be positioned in any radial direction.

Catheter 18 has a balloon 24 mounted at the distal end 22. In its inflated condition (FIG. 4), balloon 24 has a partially non-circular profile in which one part 82 of the balloon is smaller in diameter than the renal artery, whereas another part 80 of the balloon 24 is noncircular in shape. The noncircular part has a major diameter $D_{MAJ}$ equal to or just slightly less than the internal diameter of the renal artery, and has a minor diameter $D_{MIN}$ smaller than the major diameter.

An ultrasound transducer 30 (FIGS. 3 and 5) is mounted adjacent the distal end 22 of catheter 18 within balloon 24. Transducer 30, which is desirably formed from a ceramic piezoelectric material, is of a tubular shape and has an exterior emitting surface 31 in the form of a cylindrical surface of revolution about the proximal-to-distal axis 33 of the transducer 30. The transducer 30 typically has an axial length along axis 33 of approximately 2-10 mm, and preferably 6 mm. The outer diameter of the transducer 30 is approximately 1.5-3 mm in diameter, and preferably 2 mm. The physical structure of the transducer and its mounting to the catheter may be, for example, as described in U.S. Pat. Nos. 7,540,846 and 6,763,722, the disclosures of which are incorporated by reference herein. The transducer 30 also has conductive coatings (not shown) on its interior and exterior surfaces. Thus, the transducer may be physically mounted on a metallic support tube 84 (FIG. 5), which in turn is mounted to the catheter. The coatings are electrically connected to ground and signal wires 32. Wires 32 extend from the transducer 30 through a lumen 34. The lumen 34 extends between the proximal end and the distal end of a catheter 18, while the wires 32 extend from the transducer 30, through the lumen 34, to the proximal end 21 of the catheter 18.

Transducer 30 is arranged so that ultrasonic energy generated in the transducer is emitted principally from the exterior emitting surface. Thus, the transducer may include features arranged to reflect ultrasonic energy directed toward the interior of the transducer so that the reflected energy reinforces the ultrasonic vibrations at the exterior surface. For example, support tube 84 and transducer 30 may be configured so that the interior surface of the transducer 30 is spaced apart from the exterior surface of the support tube, which is formed from metal, by a gap (not shown). The distance across the gap, between the interior surface of the transducer and the exterior surface of the support tube may be one half the wavelength of the ultrasound energy emitted by the transducer, to promote efficient operation of the transducer 30. In this embodiment, the ultrasound energy generated by the transducer 30 is reflected at the water gap to reinforce ultrasound energy propagating from the transducer 30, thereby ensuring the ultrasound energy is directed outwardly from an external surface of the transducer 30.

Transducer 30 is also arranged to convert ultrasonic waves, impinging on the exterior emitting surface 31 into electrical signals on wires 32. Stated another way, transducer 30 can act either as an ultrasonic emitter or an ultrasonic receiver.

The transducer 30 is designed to operate, for example, at a frequency of approximately 1 MHz to approximately a few tens of MHz, and typically at approximately 9 MHz. The actual frequency of the transducer 30 typically varies somewhat depending on manufacturing tolerances. The optimum actuation frequency of the transducer may be encoded in a machine-readable or human-readable element (not shown) such as a digital memory, bar code or the like affixed to the catheter. Alternatively, the readable element may encode a serial number or other information identifying the individual catheter, so that the optimum actuation frequency may be retrieved from a central database accessible through a communication link such as the internet.

Figure 6:
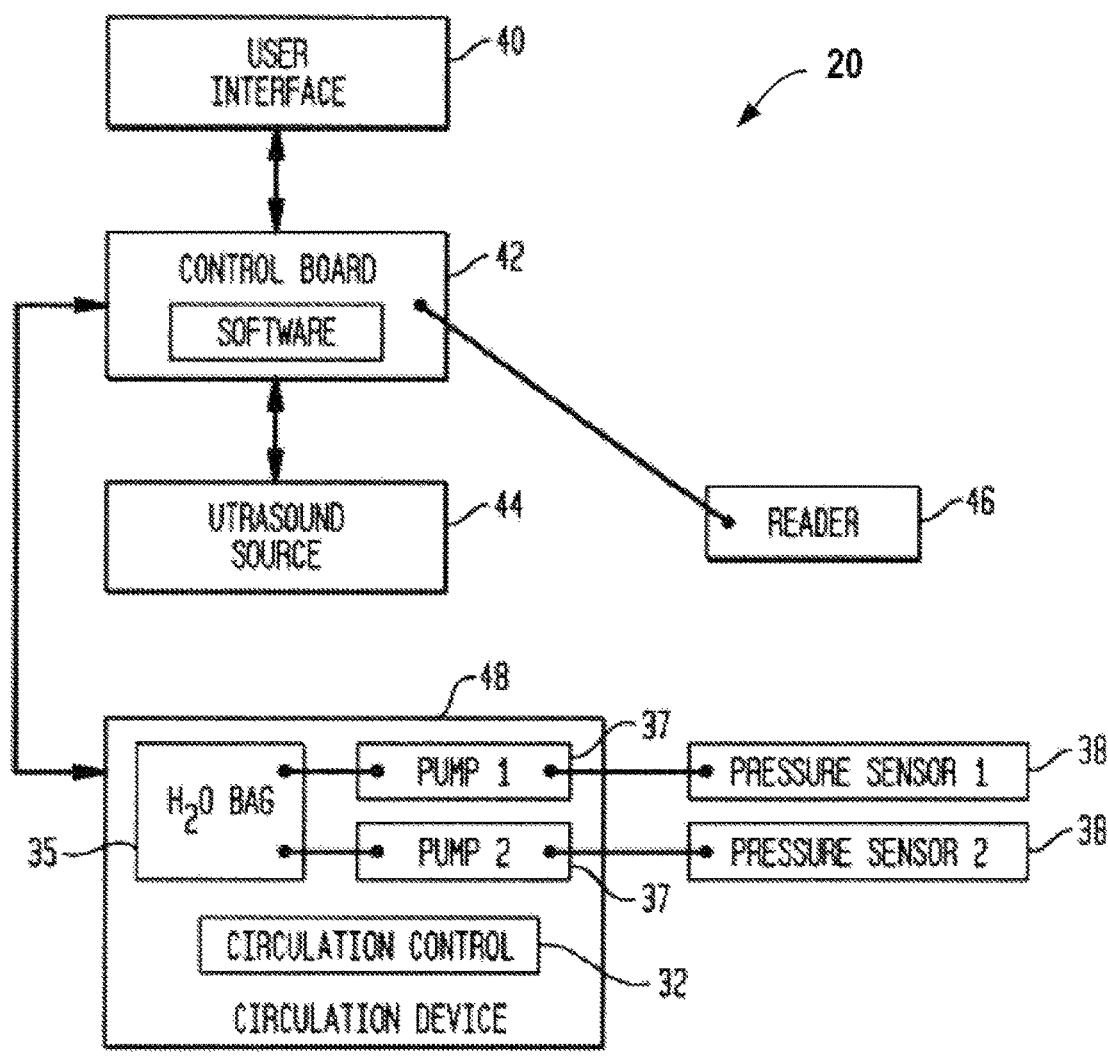
FIG. 6 is a functional, block diagrammatic view depicting portions of a component used in the apparatus of FIGS. 3 and 4.

An ultrasound system 20, also referred to herein as an actuator, is releasably connected to catheter 18 and transducer 30 through a plug connector 88 (FIG. 3). As seen in FIG. 6, ultrasound system 20 may include a user interface 40, a control board 42 incorporating a programmable control device such as a programmable microprocessor (not shown), an ultrasound excitation source 44, and a circulation device 48. The user interface 40 interacts with the control board 42, which interacts with the excitation source 44 to cause transmission of electrical signals at the optimum actuation frequency of the transducer to the transducer 30 via wires 32. The control board 42 and ultrasound source 44 are arranged to control the amplitude and timing of the electrical signals so as to control the power level and duration of the ultrasound signals emitted by transducer 30. Excitation source 44 is also arranged to detect electrical signals generated by transducer 30 and appearing on wires 32 and communicate such signals to control board 42.

The circulation device 48 is connected to lumens (not shown) within catheter 18 which in turn are connected to balloon 24. The circulation device is arranged to circulate a liquid, preferably an aqueous liquid, through the catheter 18 to the transducer 30 in the balloon 24. The circulation device 48 may include elements such as a tank for holding the circulating coolant 35, pumps 37, a refrigerating coil (not shown), or the like for providing a supply of liquid to the interior space of the balloon 24 at a controlled temperature, desirably at or below body temperature. The control board 42 interfaces with the circulation device 48 to control the flow of fluid into and out of the balloon 24. For example, the control board 42 may include motor control devices linked to drive motors associated with pumps for controlling the speed of operation of the pumps 37. Such motor control devices can be used, for example, where the pumps 37 are positive displacement pumps, such as peristaltic pumps. Alternatively or additionally, the control circuit may include structures such as controllable valves connected in the fluid circuit for varying resistance of the circuit to fluid flow (not shown). The ultrasound system 20 may further include two pressure sensors 38, to monitor the liquid flow through the catheter 18. One pressure sensor monitors the flow of the liquid to the distal catheter 18 to determine if there is a blockage while the other monitors leaks in the catheter 18. While the balloon is in an inflated state, the pressure sensors 38 maintain a desired pressure in the balloon preferably at approximately 3 pounds per square inch (20 KPa).

The ultrasound system 20 incorporates a reader 46 for reading a machine-readable element on catheter 18 and conveying the information from such element to control board 46. As discussed above, the machine-readable element on the catheter may include information such as the operating frequency of the transducer 30 in a particular catheter 18, and the control board 42 may use this information to set the appropriate frequency for exciting the transducer. Alternatively, the control board may be arranged to actuate excitation source 44 to measure the transducer operating frequency by energizing the transducer at a low power level while scanning the excitation frequency over a pre-determined range of frequencies for example 8.5 Mhz-9.5 Mhz, and monitoring the response of the transducer to such excitation.

The ultrasonic system 20 may be similar to that disclosed in U.S. Provisional Patent Application No. 61/256,002, filed Oct. 29, 2009, entitled "METHOD AND APPARATUS FOR PERCUTANEOUS TREATMENT OF MITRAL VALVE REGURGITATION (PMVR)," the disclosure of which is incorporated by reference herein.

Figure 7:
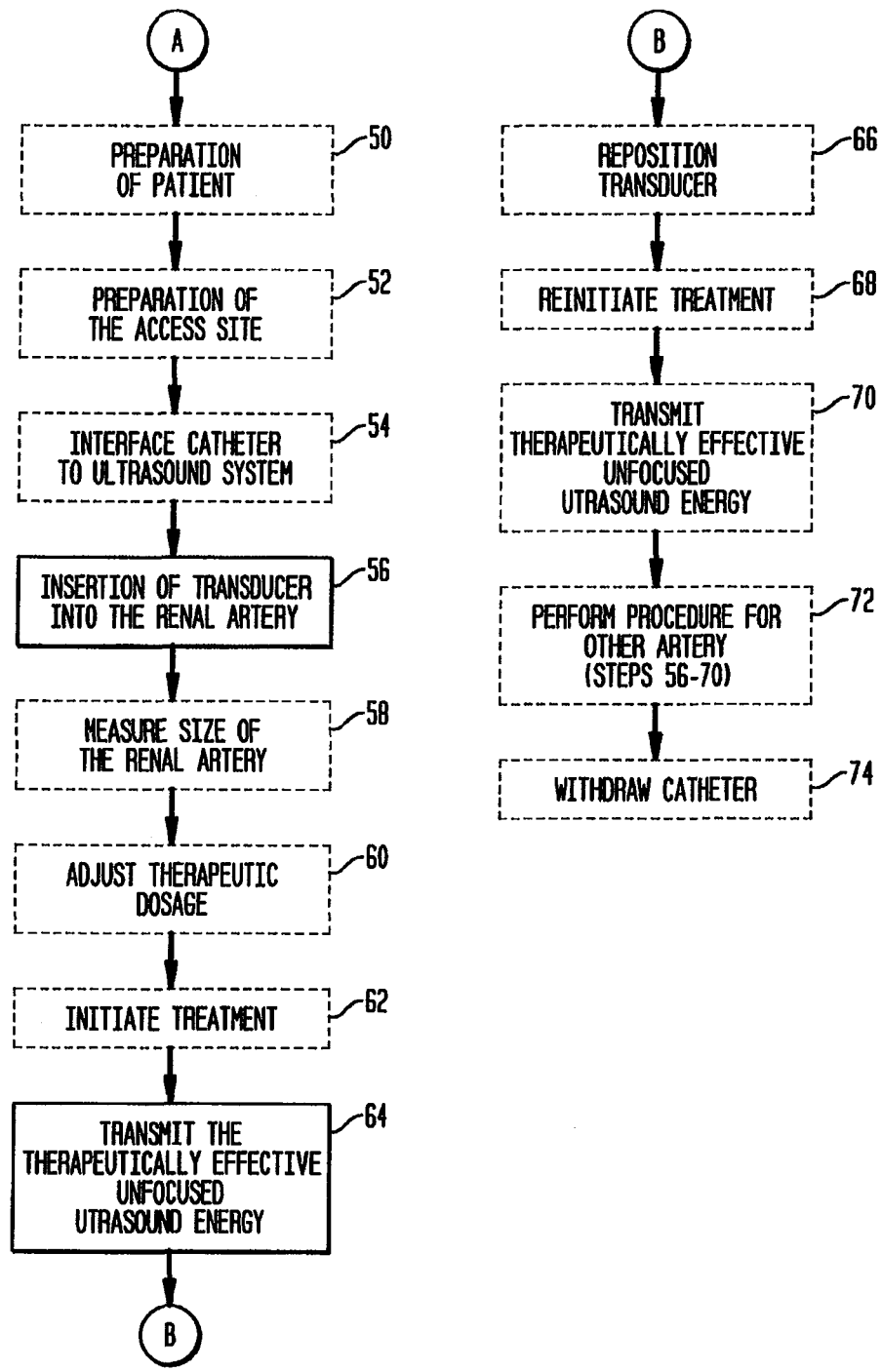
FIG. 7 is a flow chart depicting the steps used in a method according to one embodiment of the present invention.
Figure 8:
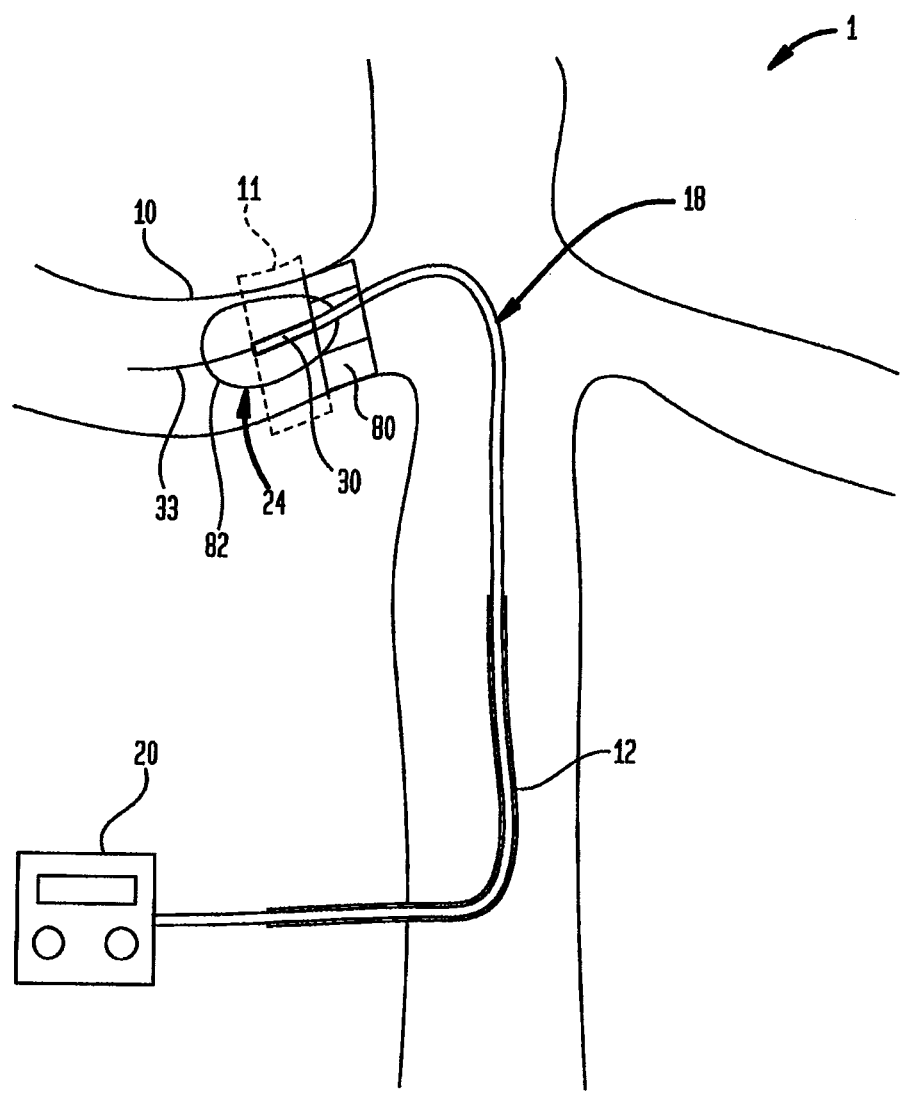
FIG. 8 is a diagrammatic view depicting portions of the apparatus of FIGS. 3 and 4 during operation in accordance with the method of FIG. 7.

A method according to an embodiment of the present invention is depicted in flowchart form in FIG. 7. After preparing a human or non-human mammalian subject such as a patient (step 50), preparation of an arterial access site such as a location on the femoral artery (step 52), and connecting the catheter 18 to the ultrasound system 20 (step 54), the ultrasound transducer 30 in inserted into the renal artery (step 56) by inserting the distal end of the sheath 12 through the access site into the aorta. While the distal end of the sheath is positioned within the aorta, the catheter 18 is advanced within the sheath until the distal end of the catheter projects from the sheath as schematically depicted in FIG. 8. Because the distal end 22 of the catheter 18 is preformed like a hook, the distal end 22 of the catheter 18 may slide into the renal artery 10 when the tip is rotated inside the aorta towards the renal artery 10 branches and then slightly pushed forward and pulled backwards. This action is facilitated by the typical angle of the renal artery/aorta bifurcation. Based on the hooked shape of the distal end 22, the distal end 22 of the catheter 18 may tend to catch in the renal artery 10 side branch when pulled back inside the aorta. The balloon 24 on the catheter desirably is maintained in a deflated condition until the distal end of the catheter is disposed at a desired location within the renal artery. During insertion of the catheter 18 and the transducer 30 (step 56), the physician may verify the placement of the transducer 30 to be within the renal artery 10, although before the kidney 6 or any branches of the renal artery 10 that may exist. Such verification can be obtained using x-ray techniques such as fluoroscopy.

Figure 4:
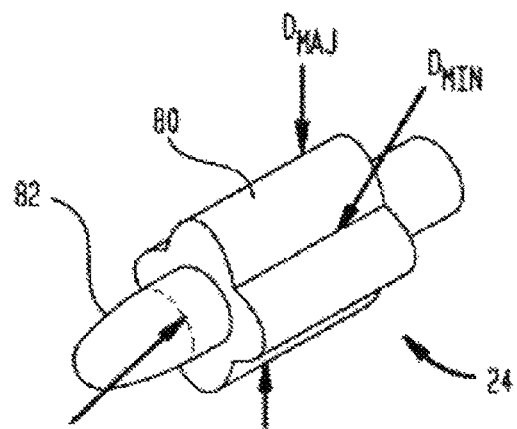
FIG. 4 is a fragmentary diagrammatic perspective view depicting a portion of the apparatus shown in FIG. 3.
Figure 5:
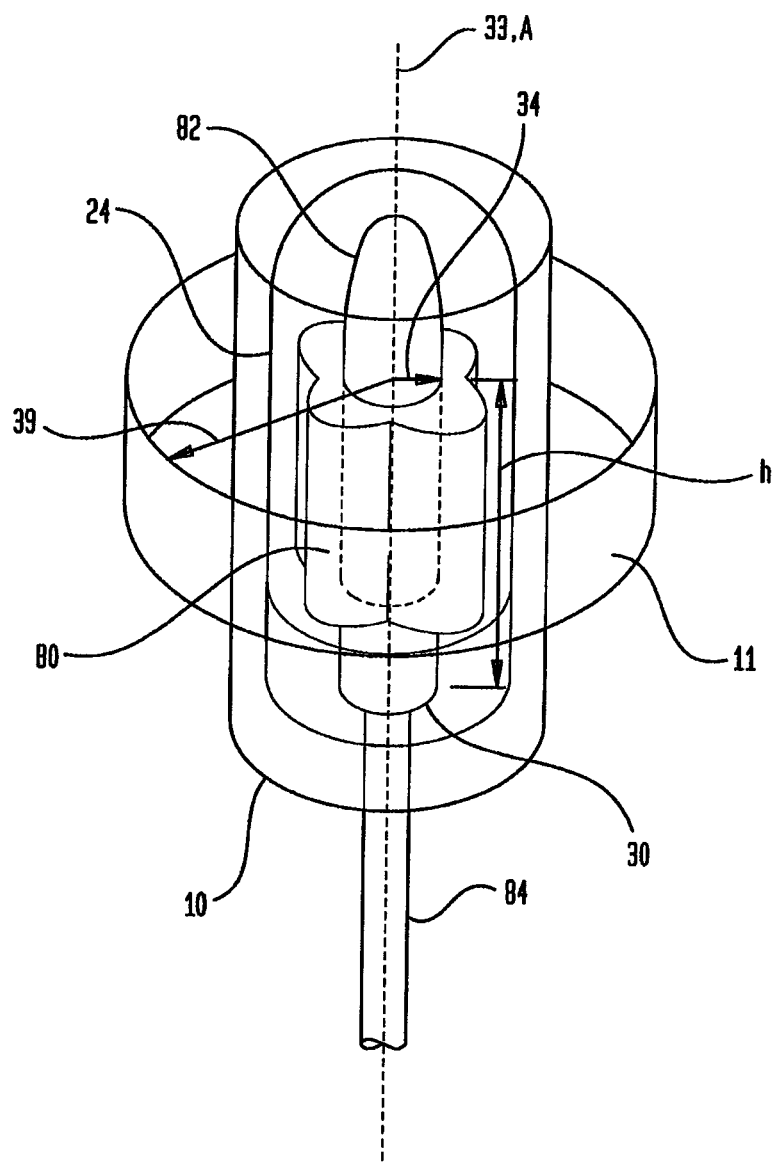
FIG. 5 is a diagrammatic view depicting a portion of the apparatus of FIGS. 3 and 4 in conjunction with a renal artery.

Once the distal end of the catheter is in position within a renal artery, pumps 37 bring balloon 24 to an inflated condition as depicted in FIGS. 4 and 5. In this condition, the non-circular portion 80 of the balloon engages the artery wall, and thus centers transducer 30 within the renal artery, with the axis 33 of the transducer (FIG. 5) approximately coaxial with the axis A of the renal artery. However, the balloon does not block blood flow through the renal artery. In this condition, the circulation device 48 maintains a flow of cooled aqueous liquid into and out of balloon 24, so as to cool the transducer 30. The cooled balloon also tends to cool the interior surface of the renal artery. Moreover, the continued flow of blood through the renal artery helps to cool the interior surface of the renal artery. The liquid flowing within the balloon may include a radiographic contrast agent to aid in visualization of the balloon and verification of proper placement.

In the next step 58, the ultrasound system 20 uses transducer 30 to measure the size of the renal artery 10. Control board 42 and ultrasound source 44 actuate the transducer 30 to "ping" the renal artery 10 with a low-power ultrasound pulse. The ultrasonic waves in this pulse are reflected by the artery wall onto transducer 30 as echoes. Transducer 30 converts the echoes to echo signals on wires 32. The ultrasound system 20 then determines the size of the artery 10 by analyzing the echo signals. For example, the ultrasound system 20 may determine the time delay between actuation of the transducer to produce the "ping" and the return of echo signals. In step 60, the ultrasound system 20 uses the measured artery size to set the acoustic power to be delivered by transducer 30 during application of therapeutic ultrasonic energy in later steps. For example, control board 42 may use a lookup table correlating a particular echo delay (and thus artery diameter) with a particular power level. Generally, the larger the artery diameter, the more power should be used. Variations in the shape of the renal artery 10, or in the centering of the transducer 30, may cause a range of time delay in the echo signals. The ultrasound system 20 may take an average of the range to determine the average size of the renal artery 10 and make adjustments to the power level based on the average size.

The physician then initiates the treatment (step 62) through the user interface 40. In the treatment (step 64), the ultrasonic system or actuator 20, and particularly the control board 42 and ultrasonic source 44, actuate transducer 30 to deliver therapeutically effective ultrasonic waves to an impact volume 11 (FIG. 5). The ultrasound energy transmitted by the transducer 30 propagates generally radially outwardly and away from the transducer 30 encompassing a full circle, or 360° of arc about the proximal-to-distal axis 33 of the transducer 30 and the axis A of the renal artery.

The selected operating frequency, unfocused characteristic, placement, size, and the shape of the ultrasound transducer 30 allows the entire renal artery 10 and renal nerves to lie within the "near field" region of the transducer 30. Within this region, an outwardly spreading, unfocused omni-directional (360°) cylindrical beam of ultrasound waves generated by the transducer 30 tends to remain collimated and has an axial length approximately equal to the axial length of the transducer 30. For a cylindrical transducer, the radial extent of the near field region is defined by the expression $L^2/\lambda$, where L is the axial length of the transducer 30 and $\lambda$ is the wavelength of the ultrasound waves. At distances from the transducer 30 surface greater than $L^2/\lambda$, the beam begins to spread axially to a substantial extent. However, for distances less than $L^2/\lambda$, the beam does not spread axially to any substantial extent. Therefore, within the near field region, at distances less than $L^2/\lambda$, the intensity of the ultrasound energy decreases linearly, in proportion to distance from the transducer 30 surface, as the unfocused beam spreads radially. As used in this disclosure, the term "unfocused" refers to a beam, which does not increase in intensity in the direction of propagation of the beam away from the transducer 30.

The impact volume 11 is generally cylindrical and coaxial with the renal artery. It extends from the transducer surface to an impact radius 39, where the intensity of the ultrasonic energy is too small to heat the tissue to the temperature range that will cause inactivation of the renal nerves 8. The impact radius 39 is determined by the dosage of ultrasound energy transmitted from the transducer 30. The volume V of impact volume 11 is determined by the following equation:

$$V=\pi r_2^2 h - \pi r_1^2 h$$

where
$r_1$=the radius of the transducer 30
$r_2$=the radius of the impact zone 11
h=length of the transducer 30

As discussed above, the length of the transducer 30 may vary between 2 mm and 10 mm, but is preferably 6 mm to provide a wide inactivation zone of the renal nerves. The diameter of the transducer 30 may vary between 1.5 mm to 3.0 mm, and is preferably 2.0 mm. The dosage is selected not only for its therapeutic effect, but also to allow the radius 39 of the impact volume 11 to be between preferably 5 mm to 7 mm in order to encompass the renal artery 10, and adjacent renal nerves, all of which lie within an average radius of 3-4 mm, without transmitting damaging ultrasound energy to structures beyond the renal artery 10. This will result in an impact volume 11 of at least 0.5 cm$^3$, with the length of renal nerve inactivation closely corresponding to the length of the transducer 32.

The power level desirably is selected so that throughout the impact volume, solid tissues are heated to about 42° C. or more for at several seconds or more, but desirably all of the solid tissues, including the intima of the renal artery remain well below 65° C. Thus, throughout the impact region, the solid tissues (including all of the renal nerves) are brought to a temperature sufficient to inactivate nerve conduction but below that which causes rapid necrosis of the tissues.

Figure 2:
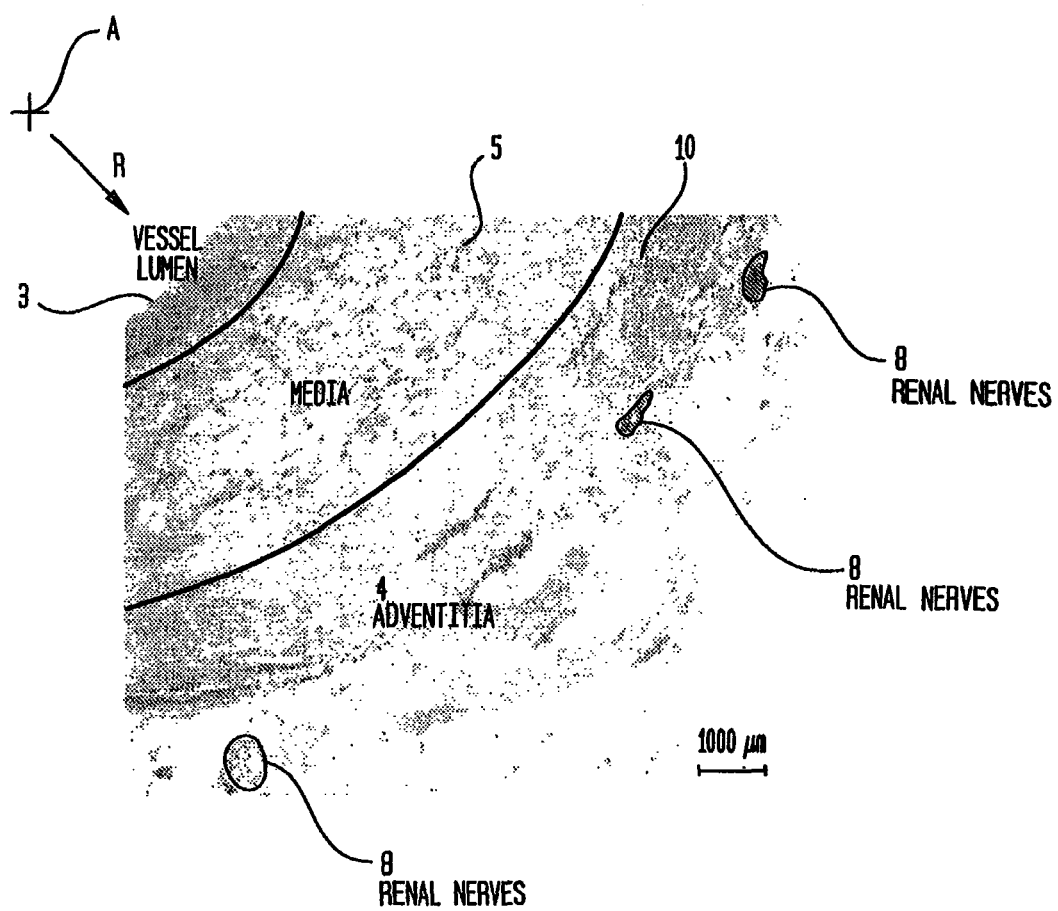
FIG. 2 is a diagrammatic sectional view depicting a portion of a renal artery and nerves.

Research shows that nerve damage occurs at much lower temperatures and much faster than tissue necrosis. See Bunch, Jared. T. et al. "Mechanisms of Phrenic Nerve Injury During Radiofrequency Ablation at the Pulmonary Vein Orifice, *Journal of Cardiovascular Electrophysiology*, Volume 16, Issue 12, pg. 1318-1325 (Dec. 8, 2005), incorporated by reference herein. Since, necrosis of tissue typically occurs at temperatures of 65° C. or higher for approximately 10 sec or longer while inactivation of the renal nerves 8 typically occurs when the renal nerves 8 are at temperatures of 42° C. or higher for several seconds or longer, the dosage of the ultrasound energy is chosen to keep the temperature in the impact volume 11 between those temperatures for several seconds or longer. The dosage of ultrasonic energy desirably is also less than that required to cause substantial shrinkage of collagen in the impact volume. Operation of the transducer thus provides a therapeutic dosage, which inactivates the renal nerves 8 without causing damage to the renal artery 10, such as, stenosis, intimal hyperplasia, intimal necrosis, or other injuries that would require intervention. The continued flow of blood across the inside wall of the renal artery 10 ensures the intimal layer 3 (FIG. 2) of the renal artery is cooled. This allows the ultrasound energy transmitted at the therapeutic dosage to be dissipated and converted to heat principally at the outer layers of the renal artery 10 and not at the intimal layer 3. In addition, the circulation of cooled liquid through the balloon 24 containing the transducer 30 may also help reduce the heat being transferred from the transducer 30 to the intimal layer 3 and to the blood flowing past the transducer. Hence, the transmitted therapeutic unfocused ultrasound energy does not damage the intima and does not provoke thrombus formation, providing a safer treatment.

In order to generate the therapeutic dosage of ultrasound energy, the acoustic power output of the transducer typically is approximately 10 watts to approximately 100 watts, more typically approximately 20 to approximately 30 watts. The duration of power application typically is approximately 2 seconds to approximately a minute or more, more typically approximately 10 seconds to approximately 20 seconds. The optimum dosage used with a particular system to achieve the desired temperature levels may be determined by mathematical modeling or animal testing.

The impact volume 11 of the unfocused ultrasound energy encompasses the entire renal artery 10, including the adventitia and closely surrounding tissues, and hence encompasses all of the renal nerves surrounding the renal artery. Therefore, the placement in the renal artery 10 of the transducer 30 may be indiscriminate in order to inactivate conduction of all the renal nerves 8 surrounding the renal arteries 10 in the subject. As used in this disclosure "indiscriminate" and "indiscriminately" mean without targeting, locating, or focusing on any specific renal nerves.

Optionally, the physician may then reposition the catheter 18 and transducer 30 along the renal artery (step 66) and reinitiate the treatment (step 68) to retransmit therapeutically effective unfocused ultrasound energy (step 70). This inactivates the renal nerves at an additional location along the length of the renal artery, and thus provides a safer and more reliable treatment. The repositioning and retransmission steps optionally can be performed multiple times. Next the physician moves the catheter 18 with the transducer 30 to the other renal artery 10 and performs the entire treatment again for that artery 10 (step 72). After completion of the treatment, the catheter 18 is withdrawn from the subject's body (step 74).

Numerous variations and combinations of the features discussed above can be utilized. For example, the ultrasound system 20 may control the transducer 30 to transmit ultrasound energy in a pulsed function during application of therapeutic ultrasonic energy. The pulsed function causes the ultrasound transducer 30 to emit the ultrasound energy at a duty cycle of, for example, 50%. Pulse modulation of the ultrasound energy is helpful in limiting the tissue temperature while increasing treatment times.

In a further variant, the steps of measuring the renal artery size and adjusting the dose (steps 58 and 72) may be omitted. In this instance, the transducer is simply operated at a preset power level sufficient for the renal arteries of an average subject. In a further variant, the renal artery diameter can be measured by techniques other than actuation of transducer 30 as, for example, by radiographic imaging using a contrast agent introduced into the renal artery or magnetic resonance imaging or use of a separate ultrasonic measuring catheter. In this instance, the data from the separate measurement can be used to set the dose.

In the particular embodiment discussed above, the transducer 30 is centered in the renal artery by the non-circular element 80 of expansible balloon 24. Other centering arrangements can be used. For example, an expansible balloon encompassing the transducer may be a balloon of circular cross-section slightly smaller in diameter than the renal artery 10. Such a balloon allows blood to continue to flow through the renal artery 10, but maintains the transducer 30 roughly centered in the renal artery 10. In this embodiment, the balloon 24 is dynamic rather than fitted to the renal artery 10 because the flow of blood around the balloon 24 causes small back and forth movements. This dynamic nature allows the blood to continue to reach all parts of the renal artery 10, thereby providing cooling and minimizing damage to the intima 3. In other embodiments, the distal end of the catheter can include expansible structures other than balloons, such as a wire basket or wire mesh structure which can be selectively brought to a radially expanded condition, such as by compressing the structure in the axial direction. The wire basket may be non-reflecting to ultrasound, or may be mounted on the catheter at a position axially offset from the transducer 30.

In a further variant, the balloon 24 may be formed from a porous membrane or include holes, such that cooled liquid being circulated within the balloon 24 may escape or be ejected from the balloon 24 into the blood stream within the renal artery 10. The escaping or ejected cooled liquid from the balloon 24 that enters the blood flow may support further cooling of the inner lining of the renal artery 10, which is in contact with the flowing blood.

Typically, catheter 18 is a disposable, single-use device. The catheter 18 or ultrasonic system 20 may contain a safety device that inhibits the reuse of the catheter 18 after a single use. Such safety devices per se are known in the art.

In yet another variant, the catheter 18 itself may include a steering mechanism which allows the physician to directly steer the distal end 22 of the catheter. The sheath may be omitted.

Another variation may be that an energy emitter unit at the distal end of the catheter 18, which includes the ultrasound transducer 30, may be positioned in the renal vein, and the ultrasound transducer 30 may include reflective or blocking structures for selectively directing ultrasound energy from the transducer 30 over only a limited range of radial directions to provide that ultrasound energy desirably is selectively directed from the transducer 30 in the renal vein toward the renal artery 10. When the venous approach is utilized, the ultrasound energy is directed into a segment or beam propagating away from an exterior surface of the transducer 30, commonly known as a side firing transducer 30 arrangement. For example, the ultrasound transducer 30 may have a construction and be operated to emit directed ultrasound energy 5 similarly as disclosed in U.S. Provisional Application No. 61/256,002, filed Oct. 29, 2009, entitled "METHOD AND APPARATUS FOR PERCUTANEOUS TREATMENT OF MITRAL VALVE REGURGITATION (PMVR)," incorporated by reference herein. In this variation, the route by which the catheter 18 is introduced into the body, and then positioned close to the kidneys 6, is varied from the atrial approach discussed above. A venous approach may be utilized to take advantage of the potential for reduced closure issues after catheter 18 withdrawal.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A method for inactivating renal nerve conduction in a mammalian subject, the method comprising:
    inserting an ultrasound transducer into a renal artery of the mammalian subject, wherein the ultrasound transducer is positioned along a distal end of a catheter, the catheter comprising a balloon mounted along the distal end of the catheter such that the ultrasound transducer is disposed within the balloon;
    inflating the balloon such that the balloon engages an inner wall of the renal artery and the ultrasound transducer is positioned within the renal artery;
    delivering cooled liquid to the balloon to cool an intima layer of the renal artery; and
    actuating the ultrasound transducer to cause the ultrasound transducer to emit a therapeutic dose of unfocused ultrasound energy through the intima layer and into an impact volume of at least 0.5 cm$^3$ disposed in an adventitia layer comprising renal nerves of the renal artery to inactivate conduction of the renal nerves in the impact volume without causing damage to the intima layer of the renal artery.

2. The method of claim 1, wherein actuating the ultrasound transducer to cause emission of the therapeutic dose of unfocused ultrasound energy is performed so as to maintain a temperature of the inner wall of the renal artery below 65° C. while heating the renal nerves in the impact volume to above 42° C.

3. The method of claim 1, wherein inserting the ultrasound transducer and actuating the ultrasound transducer to cause emission of the therapeutic dose of unfocused ultrasound energy are performed without determining actual locations of the renal nerves.

4. The method of claim 1, wherein the therapeutic dose of unfocused ultrasound energy is emitted in a 360° cylindrical pattern surrounding the ultrasound transducer.

5. The method of claim 1, wherein the therapeutic dose of unfocused ultrasound energy is emitted in a pattern having a length of at least 2 mm along an axis of the renal artery.

6. The method of claim 1, wherein the therapeutic dose of unfocused ultrasound energy inactivates conduction of a length of at least 2 mm of the renal nerves.

7. The method of claim 1, further comprising positioning the ultrasound transducer out of contact with the inner wall of the renal artery at least when the balloon is inflated.

8. The method of claim 1, further comprising applying the unfocused ultrasound energy throughout the impact volume at a level insufficient to cause necrosis of tissues.

9. The method of claim 1, wherein the impact volume encompasses all of the renal nerves surrounding the renal artery.

10. The method of claim 1, wherein actuating the ultrasound transducer to cause emission of the therapeutic dose of unfocused ultrasound energy comprises emitting the therapeutic dose of unfocused ultrasound energy from the ultrasound transducer at an acoustic power level of 10 to 30 watts for 2 seconds to a minute.

11. The method of claim 1, further comprising:
    receiving ultrasound energy;
    generating a signal representing the received ultrasound energy;
    emitting unfocused ultrasound energy at a measurement level;
    receiving an echo signal representing reflected measurement ultrasound energy; and
    analyzing the received echo signal.

12. The method of claim 11, further comprising determining a size of the renal artery based on the received echo signal and varying acoustic power of the ultrasound energy used to emit the unfocused ultrasound energy depending on the determined size of the renal artery.

13. The method of claim 11, further comprising determining the therapeutic dose based on the echo signal by measuring a time delay between an actuation of the ultrasound transducer and a return of the echo signal and determining the therapeutic dose using a lookup table showing a relationship between the time delay and the therapeutic dose.

14. The method of claim 1, wherein the impact volume is generally cylindrical and coaxial with the renal artery.

15. The method of claim 1, further comprising determining a volume (V) of the impact volume by: $V = \pi r_2^2 h - \pi r_1^2 h$, where $r_1$ is the radius of the ultrasound transducer, $r_2$ is the radius of the impact volume, and h is the length of the ultrasound transducer.

16. The method of claim 1, wherein the cooled liquid delivered to the balloon comprises a radiographic contrast agent.

17. The method of claim 16, further comprising visualizing the radiographic contrast agent to verify proper placement within the renal artery using radiographic imaging.

18. The method of claim 1, further comprising repositioning the ultrasound transducer along the renal artery and re-actuating the ultrasound transducer to cause the ultrasound transducer to emit another therapeutic dose of unfocused ultrasound energy.

19. The method of claim 1, further comprising:
removing the ultrasound transducer from the renal artery;
inserting the ultrasound transducer into a second renal artery; and
re-actuating the ultrasound transducer to cause the ultrasound transducer to emit another therapeutic dose of unfocused ultrasound energy.

20. The method of claim 1, wherein the balloon has a profile and the profile of the balloon is non-circular.

21. The method of claim 1, wherein actuating the ultrasound transducer to cause emission of the therapeutic dose of unfocused ultrasound energy comprises emitting the therapeutic dose of unfocused ultrasound energy at a power level of 10 to 30 watts for 2 to 30 seconds.

22. The method of claim 1, wherein actuating the ultrasound transducer to cause emission of the therapeutic dose of unfocused ultrasound energy comprises emitting the therapeutic dose of unfocused ultrasound energy from the ultrasound transducer at a frequency of 1 to 30 MHz.

* * * * *